United States Patent [19]

Dory

[11] 4,063,451

[45] Dec. 20, 1977

[54] SCANNING

[75] Inventor: Jacques Dory, Meaux, France

[73] Assignee: Realisations Ultrasoniques, France

[21] Appl. No.: 572,790

[22] Filed: Apr. 29, 1975

[30] Foreign Application Priority Data

Apr. 29, 1974   France ................................ 74.14930

[51] Int. Cl.² .......................................... G01N 29/00
[52] U.S. Cl. ...................................... 73/618; 73/901; 358/112
[58] Field of Search ...................... 73/67, 67.5 R, 67.7, 73/67.6, 67.8 R, 67.8 S, 67.9, 71.5 US; 315/9, 13, 31 R; 340/5 MP, 1 R, 3 R; 358/112; 343/17

[56] References Cited

U.S. PATENT DOCUMENTS

| | | | |
|---|---|---|---|
| 2,602,921 | 7/1952 | Peters et al. ............................... | 315/9 |
| 2,718,609 | 9/1955 | Covely ....................................... | 315/9 |
| 2,957,340 | 10/1960 | Rocha ....................................... | 73/67.5 R |
| 3,260,887 | 7/1966 | Alexander et al. ....................... | 315/9 |
| 3,534,590 | 10/1970 | Kent et al. ............................... | 73/67.5 |
| 3,554,186 | 1/1971 | Leksell ..................................... | 73/67.9 |
| 3,778,614 | 12/1973 | Hounsfield ........................ | 73/67.5 R |
| 3,864,661 | 2/1975 | Ranalli ................................. | 73/67.7 |

OTHER PUBLICATIONS

Becker et al. *Ultrasonic Isometric Imaging*, Proceedings of Society of Photo-Optical Instrumentation, Feb. 1972, pp. 61-65.

*Primary Examiner*—Richard C. Queisser
*Assistant Examiner*—Stephen A. Kreitman
*Attorney, Agent, or Firm*—William Anthony Drucker

[57] ABSTRACT

In a system of analysis of an object or a body by means of "transgraphy" i.e. of radiography by transmission, wherein a receiver transducer and a transmitter transducer are linearly and angularly synchronously displaced, the signal supplied by the receiver transducer modulates one characteristic magnitude—intensity or velocity—of the spot of an electronic tube including a charge storage and memory element, while one line scanned by said spot corresponds to a fixed position of the assembly of transmitter and receiver transducers.

9 Claims, 6 Drawing Figures

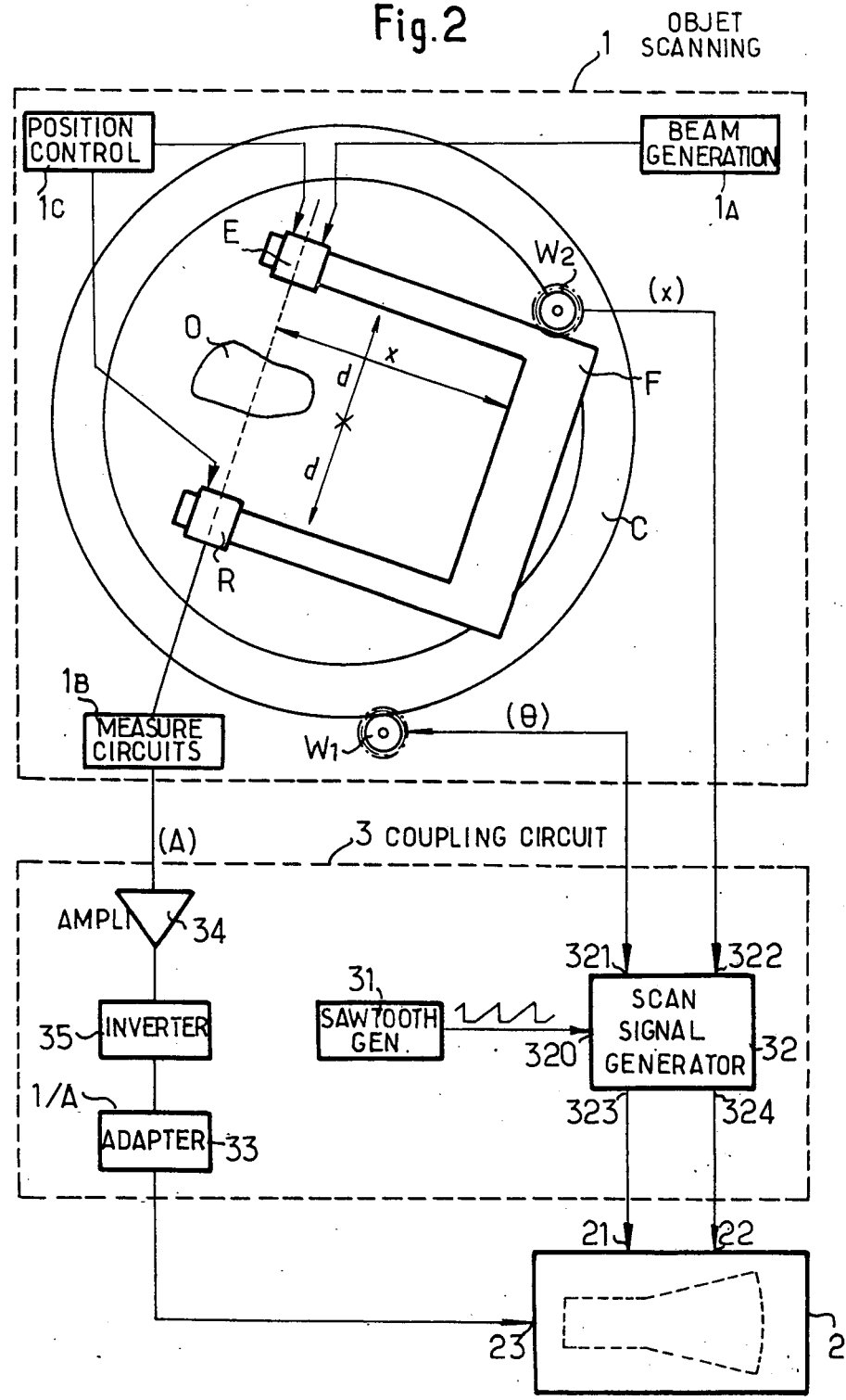

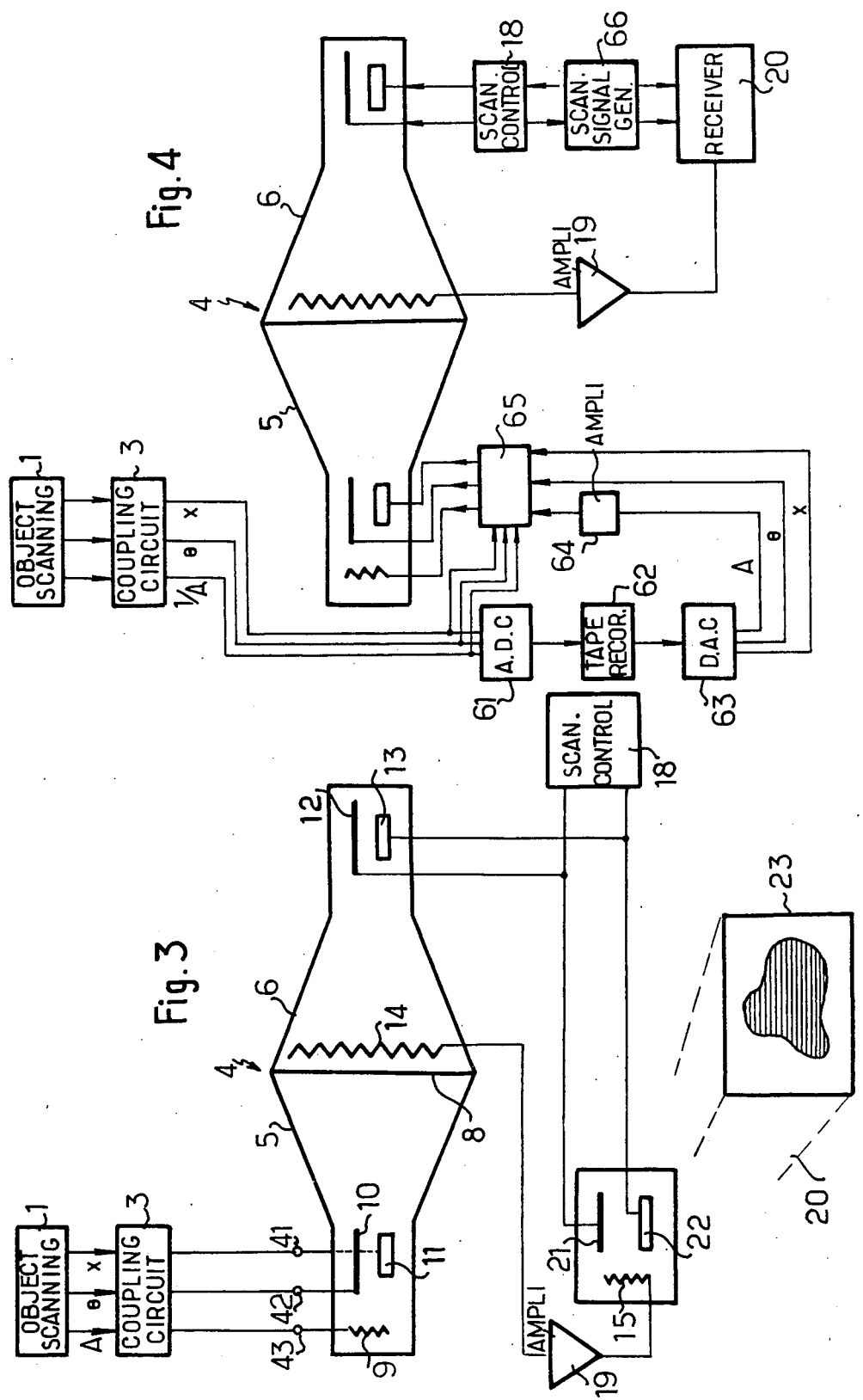

SCANNING

The present invention relates to the examination of an object by successively scanning the latter by means of a wave radiating beam, the orientation of which is modified from one scan to the other.

The internal structure of the object is deduced from the measurement of the absorption undergone by the beam.

This type of examination is used particularly in medicine for the examination of the brain.

Up to now the exploitation of the absorption measurements was effected numerically, generally by means of numerical computers.

This exploitation procedure, which supplies highly accurate results, is long, costly and inconvenient which sometimes make its use prohibitive. For example, it already takes several minutes to count an image whose resolution does not exceed 180 × 180 points, and the price of the computer easily attains 50% and more of the total price of the installation.

The object of the present invention is to eliminate these inconveniences by supplying directly, from the absorption measurements, the luminous image of the internal structure of the object examined in the plane of examination. The image, formed gradually in the course of the scanning, is completed at the end of the latter. Several planes can then be explored successively, and the decision of these successive explorations can be made according to the results of the first examinations.

Another advantage of the invention is that it supplies a relatively inexpensive exploitation device. By using ultrasonic waves, for example, for the exploration, a highly advantageous analysis system was obtained.

The exploitation systems according to the invention are characterized by a device having writing means and recording means capable of charge storage and memorization and means for coupling said device to the scanning means of the examination beam and to means for measuring the weakening undergone by the latter.

According to a preferred embodiment of the invention, the said device comprises a cathode ray tube with charge storage and memory of the type with writing and reading guns, and it is coupled directly to a television receiver of the monitor type, the video signal of the latter being modulated by the reading signal of the target of the cathode ray tube.

According to an improvement of the invention, the weakening data of the beam are recorded, for example, in numerical form on magnetic cassettes; they are then passed at high speed over the tube. This permits reexamination of each image as long and as often as necessary by regulating the gain according to the examined zone, and defining, if necessary, the zones of the object where a finer scanning and or scanning in other planes would be desirable.

The understanding of the invention will be facilitated by the following description and the figures wherein:

FIG. 2 is the principal diagram of an improved examination device according to the invention;

Figure 5:
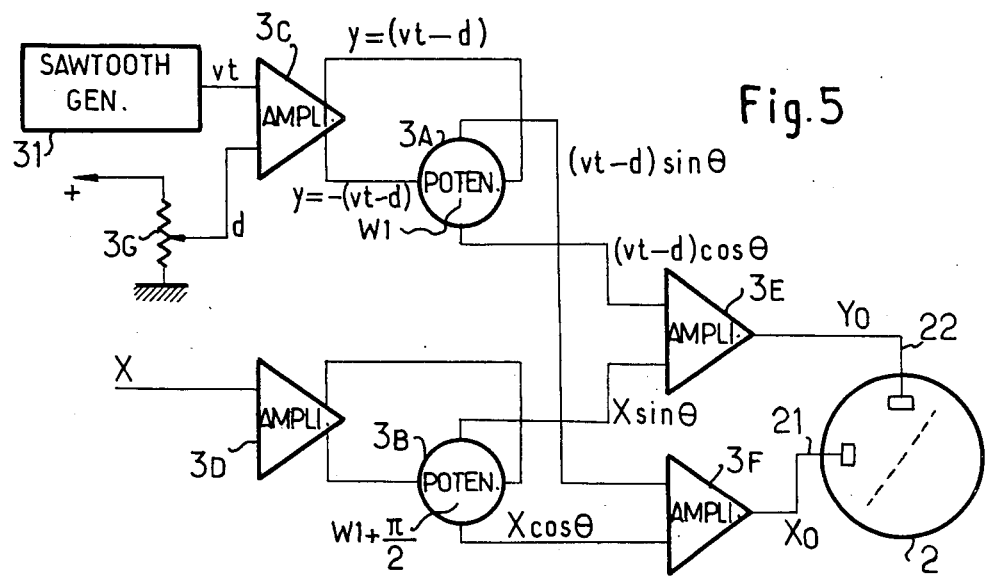
Figure 6:
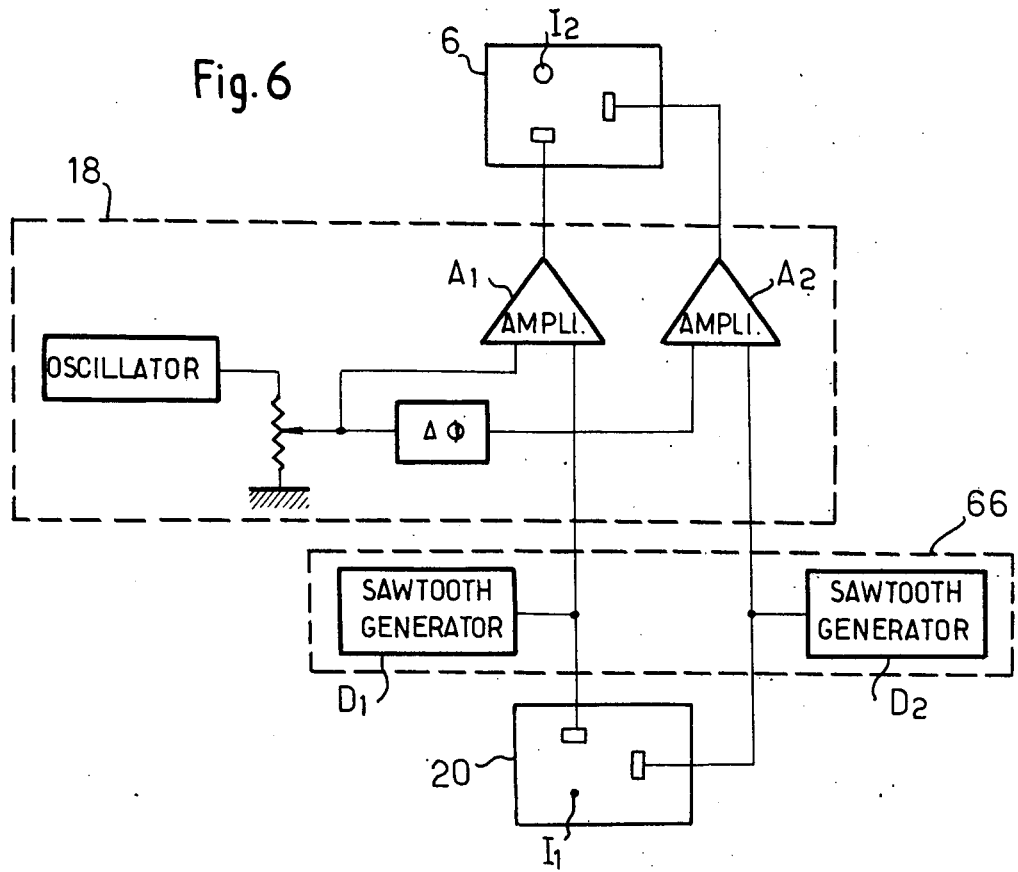

FIGS. 3 and 4 are variations of the embodiment of the visual display circuit according to the invention, and FIGS. 5 and 6 are preferred diagrams of certain elements of the circuits of FIGS. 2 and 4 respectively.

Figure 1:
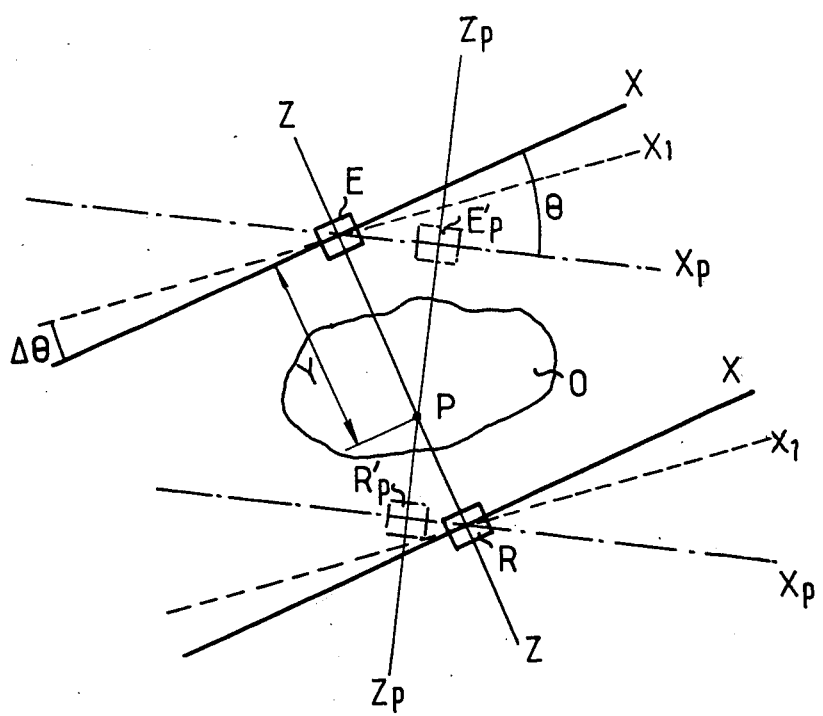
FIG. 1 is a diagram illustrating the scanning principle of the object effected in the system to which the invention refers.

We see in FIG. 1 in E and R respectively the sound transmitter and sound receiver of a "transgraphic" system, that is, radiography by conventional transmission. These sounds are placed facing each other on either side of the examiner object O. The sound transmitter E transmits a fine beam extending along the axis ZZ connected to sound transmitter E. The radiation can be of any type (X-rays, ultrasonic, infrared..), it being important only that the radiation received in receiver R is as fine as possible. The amplitude A of the radiation received in receiver R is permanently measured. The characteristic parameter of the structure of the object O being the ratio $A/Ao$, where $Ao$ is the amplitude of the transmitted radiation, it being indispensable, if the single measurement of A is to be sufficient to characterize the object, that $Ao$ is rigorously constant. One could free oneself of this limitation at the expense of measuring circuits for $Ao$ and calculating the ratio $A/Ao$, circuits whose assembly would be more complex than those necessary for the regulation of the transmission. The probes E and R are displaced simultaneously in the same plane along two lines X perpendicular to the axis ZZ, so that the beam scans the entire object O. After each scanning, the axis ZZ is turned by an angle $\Delta\theta$ and a new scanning is effected. The same operation is repeated $n$ times ($n$ equals any integral number, generally over 100), until the axis ER has turned by a total of 180°. For example, we assume $\Delta\theta = 1°$, and $n = 180$. In the drawings we have represented in solid lines the translation axes X of the sounds at the origin, and in broken lines the translation axes $Xl$ after the elementary rotation of the assembly of $\Delta\theta$ and in dot-dashed lines the position of the axes $Xp$ for $p$ rotations ($p$ less than $n$), the sounds being then in $E'p$ and $R'p$ on the axes $Xp$. We could also rotate the assembly rapidly and displace E and R of $\Delta X$ at each revolution.

The principle of this examination is thus as follows: In the course of each scanning, the variations of the amplitude A of the radiation received are due to the partial absorption of the radiation by the structures traversed by the latter. In a given point P of the trajectory of the rays, that is, on the segment of the axis ZZ comprised between E and R, in a distance Y from the axis X, for a position of the assembly E and R defined by the abscissa X, counted from any fixed origin on the axis X, this absorption is the sum SIGMA ($\Sigma$) of all the elementary absorptions $da$ corresponding to each of the structures comprised between E and P or $$\Sigma = \int_o^Y da\,(y)\,dy,$$

where O is less then Y which is less than or equal to Y, $y$ being the distance from the axis X or any pointed between E and P, and Y being the thickness of the object perpendicular to the axes X. This sum is a function of X and of $\theta$. Since the measured amplitude is $A = Ao/\Sigma$, SIGMA ($\Sigma$) is a function of the X coordinate of E on the axis X, and of $\theta$; $Ao$ is constant.

We have at the end of the examination of $n$ functions of the form $A(X,\theta)$. The exploitation of this examination consists in translating these functions into coefficients of absorption for each point of the structure O.

Heretofore only mathematical solutions have been found. These solutions, using complex computations, require recourse to large ordinators, the computation is slow and onerous.

The exploitation devices of this examination according to the invention, on the other hand, use no computing circuit. Relatively simple, they are much faster and less onerous. Their principle consists substantially in the use of a charge storage and memory tube, and more generally, in the use of a device having writing means and recording means which are capable of charge storage and memory.

To each position of the exploring beam (X-ray, ultrasonic . . .) there corresponds a line scan on the tube.

The density of electrical charges deposited during the scanning is a function of the intensity transmitted through the object. It is thus constant on the same line. The regulation is so effected that the density of the charges deposited in the course of a scanning is much lower than that corresponding to the saturation of the target of the tube.

In the course of the successive scannings, the storage of the charges at the intersection of the different scan lines yields the image of the object.

Depending on the nature of the tube used, the image obtained is a luminous image (remnance tube) or not; for example, it can be an electric image (charge storage tube, for example) which is transformed into a luminous image.

An assembly for transgraphic examination, improved according to the invention, comprises thus essentially, as represented in FIG. 2, an object scanning device 1, working on the principle illustrated in FIG. 1, a recording device with writing means and recording means capable of charge storage and memory 2, for example a charge storage and memory tube, and coupling circuits 3 for coupling said recording device to the examination display tube 1. To facilitate the understanding, we will assume below that a cathode ray tube is used. The transducer E and R slide respectively on the two parallel arms of a U-shaped frame F, which is integral with a ring C that can turn in one or the other direction.

For the sake of clarity, we have represented in Ia, IB and Ic the known circuits connected with the transducer from E and R, and on the other hand, for the production of the beam (generator, power amplifier, localizing apparatus . . .) and for the measurements or the radiation received and the formation of an electric measuring signal (filter, transducers . . .) and connected to the two transducer for controlling their displacement; W1 and W2 represent schematically transmitter systems indicating the position of the examination beam; these are two gear wheels rotating about fixed axles and meshing respectively with the ring C and with an endless screw, for example, which is integral with the sound transmitter E. These wheels are coupled to electric devices (not shown), supplying an electric signal proportional to their position (potentiometers, generators, revolution counters . . .).

The coupling devices 3 are provided to ensure on the target or the screen of tube 2 a homothetic scanning in synchronism with that of the object O as a function of the absorption undergone by the exploration beam. In order to obtain the first of these functions, they comprise at least one sawtooth voltage generator 31 and one scanning signal generator 32 having an input 320 for the sawtooth signal, two inputs 321 and 322 for the signals X and θ and two outputs 323 and 324 respectively coupled to the control inputs 21 and 22 of the horizontal and vertical deflection circuits of the tube 2.

The circuit 32 supplies on lines 323 and 324 respectively two sawtooth signals with different time bases, the ratio of the velocities of the horizontal and vertical deflection being a function of the value of θ (they are only equal for θ = 45° if we start from a horizontal scan to θ = 0°) and the vertical position of the spot at the start of each line being a function X. In order to obtain the second of these functions, there is at least one adaptor 33, transforming the signal detected by sound generator R into a modulation signal of the intensity of velocity of the electron beam; preferably they also comprise an amplification circuit 34 and an inverter 35, so that the intensity of the electronic beam varies in an opposite direction to the absorption of the examination beam. This circuit is not indispensable; in its absence, the final image would be the negative of the examined structure.

Scan signal generator 32 supplies control signals which result in a scanning of the screen of tube 2 homothetic with that of the body O. If $v$ is the scan velocity of the spot or tube 23, the coordinates $X_o$, $Y_o$ in cartesian axes system of the spot at a given instant are of the form $$X_o = d \sin \theta + X \cos \theta + Vt \sin \theta$$

$$Y_o = D \cos \theta + X \sin \theta + vt \cos \theta$$

where X and θ have been defined with reference to FIGS. 1 and 2, $t$ is the time computed from the beginning of the exploration, starting from θ = 0, and $d$ is the distance computed parallel to the axis ER of the center of rotation of the system, to either axes X.

Circuits supplying scan signals are up to those skilled in the art. FIG. 5 shows by way of example a preferred embodiment of circuit 32. This circuit comprises essentially four amplifiers 3C, 3D, 3E and 3F, and two potentiometers 3A, 3B, mounted with an angular shift by $\pi/2$ with respect to each other on the shaft of devices W1 (FIG. 2). Devices P1 and P2 are controlled in synchronism with the rotation of the exploration assembly.

Differential amplifier 3C has two inputs, one of which is coupled to the output of sawtooth generator 31 and the other to a d-c source (not shown) supplying by means of a calibrated potentiometer 3G a voltage proportional to $d$.

Amplifier 3C has two symmetrical outputs coupled to potentiometer 3A, which supplies signal $(vt - d) \sin \theta$ to sum-differential amplifier 3E, amplifiers 3E and 3F receiving also respectively signals $X \sin \theta$ and $X \cos \theta$ from potentiometer 3B coupled to the output of amplifier 3D.

If the tube is a remnance tube, the structure of the body examined in the examination plane will appear in the form of a luminous image on the screen, the image being formed to the extent the scanning progresses. However, it is generally preferable to obtain on the cathode ray tube the formation of an intermediate electric image and to form the luminous image on the separate screen; for example, but not limited, on the screen of a television receiver used in television studios for monitoring broadcasts.

This latter embodiment of the invention is represented in FIG. 3; here the circuit 3 is coupled to inputs 41, 42 and 43 of the writing circuits of a storage tube 4 with two guns 5 and 6 arranged on either side of target 8 with a transparent, semiconductive memory; inputs 41 and 42 correspond to the scan inputs 21 and 22 of FIG. 2 and are coupled respectively to a vertical deflection device 10 and to a horizontal deflection device 11; input 43 corresponds to the modulation input 23 and is coupled to modulation electrode 9 of the writing spot, gun 5 being the writing gun and gun 6 being the reading gun for the image formed on the target during the scanning of the latter by the writing beam radiated by cathode 9. A scan control device 18, for example, of the television type, controls the deflection devices 12 and 13 of the reading beam of gun 6. The reading signal of target 8 by the beam of gun 6, captured by electrode 14 and amplified, if necessary, in amplifier 19, is applied to modulation electrode 15 of the spot of a television receiver 20 whose deflection control electrodes are connected to the scan signal generator 18. Under these conditions, the electric image recorded on target 8 appears in the form of a homothetic luminous image on screen 23 of the television receiver. The intensity of the writing beam of tube 4 is regulated to a very low level so that the amount of charge deposited during a passage is very small and does not give rise during the reading to an image that is visible on the screen 23. The brightest zones of the image correspond to the zones of the target where most charges are accumulated. These zones correspond to the structures which have caused the greatest weakening of the examination beam (in order not to overload the Figures, we have not shown the different amplifiers, power generators and other conventional adaptation circuits).

The demonstration is immediate in the case of an isolated absorbent point where charges are only deposited on the scan lines passing through this point.

If $\sigma$ is the intensity of the charge along a line passing through this point, we see that at the intersection of all scan lines, the charge deposited will be $n\sigma$, while it will be at best equal to $\sigma$ at any other point (in a number of different angular positions). If $n$ is large, the point of intersection of the image of the absorbent point will appear as a bright point during the reading.

The problem is more complex for a real object comprising numerous absorbent parts, but one can show by a simple calculation that the image obtained reproduces the structure of the object with a resolution and fidelity which depends on the dimension of the exploration beam and on the number $n$ of passages. The image is thus obtained to the extent of the explorations.

In practice it can be interesting to record in numerical form the different values of the modulation signal of the writing beam on magnetic cassettes, for example, to pass them then, at high speed over the memory tube. This technique permits modifying the regulation of the writing intensity between two passes to put in evidence more or less absorbent structures which can not all be reproduced correctly simultaneously because of the low dynamic range of the memory tube. In fact, if the integration properties of the memory tube 4 are excellent, charges can be deposited linearly and progressively on the target in several thousand passes, if necessary, but because of the heterogeneity of the target, the dynamic range of the reading is small and it is difficult to read the charge densities correctly in a ratio higher than 20 to 30 db. The preferably numerical recording permits display of the object, presenting a great contrast several times, the successive treatment of the information being effected with different regulation of writing circuit. The time in which an image comprising 200 × 200 points, for example, is formed, is in this case of the order of 65 seconds, the scan frequencies that can be obtained with the known tubes being higher than 150 kcs (this value corresponds to the most unfavorable case of an electromagnetic deflection tube) while the exploration of the object can take several minutes.

If the scanning of the target on the writing side is well-determined, for each value of $\theta$, as many parallel lines as values of X, the step of variation of the orientation of the lines being equal to the step $\Delta\theta$ of the variation of $\theta$, the scanning on the reading side is independent of the scanning of the object.

It is assumed in FIG. 3 that the scanning of the television screen and that of the target by the reading beam were identical and controlled by the same generator 18. In fact, it may be of interest to use different scannings. One can show that the image of a point of the object is not a point on the target, but a spot whose size is a function of the width $d$ of the examination beam. One can show in a first approximation, neglecting the width of the writing beam, that this spot comprises a central circular surface with a uniform charge density and a width $d$ surrounded by a peripheral zone, the density of which decreases rapidly as we move away from the central zone.

We know, on the other hand, that in scanning an image according to a given law and then in reproducing it by scanning according to a different law, we obtain a deformed image. If the first image was obtained from an initial image by deformation of the latter, we can restore the initial image by selecting judiciously the relation between these two scanning laws. If $H(x,y)$ is the convolution which permits passage from the initial image to the intermediate image, the two scannings must be connected by the relation H.

FIG. 4 shows the principle diagram of an elaborate exploitation assembly, comprising numerical recording and control circuits of different scannings of the reading gun and of the television spot. A numerical recording device has been selected for its precision. This is a simple recording device and has no computing circuits. The three output signals of the circuits 3 are here applied simultaneously to the writing gun of tube 4 and to an analog-digital converter 61 from where they are transmitted to a magnetic tape 62 from where they can be extracted without destruction, to be applied to gun 5 after decoding in digital-analog converter 63, the absorption signal being preferably amplified positively or negatively in the variable gain amplifier 64. The device 65 is a three-way switch which permits coupling of the writing gun to the examination device directly or delayed.

On the other hand, the scanning of the television receiver is effected here under the control of a scanning signal generator 66 according to a law differing from the scanning of the target by the reading beam; the double arrow between 18 and 66 indicates that the scanning laws are different, but in a well-defined relation.

FIG. 6 shows by way of example a preferred assembly of scan control generators 18 and 66.

It is assumed here that each point P of the object 40 gives rise to a circular spot on the target 8 of the tube 4. In this case, assuming that the TV receiver is conventionally scanned, scan control device 18 should give rise to a fast circular scanning of target 8 by the reading beam which results in a scanning spot, the center of which moves along the same displacement law as the spot of the TV receiver screen.

Generator 66 comprises two conventional sawtooth generators D1 and D2 coupled to receiver 20. Scan control 18 comprises a high frequency oscillator, the frequency of which is high enough for the oscillator to supply a great number (100 e.g.) oscillations per scanning line of receiver 20; it comprises also a $\pi/2$ phase shifter $\Delta\phi$ and two sum amplifiers A1 and A2. To amplifier A1 and A2 are applied respectively the sawtooth signal of devices D1 and D2. Amplifier A1 receives also the signal of oscillator O, e.g., a 100 MHZ signal and A2 the same signal phase shifted by device $\Delta\phi$. The outputs of amplifiers A1 and A2 are coupled to the deflection electrodes of gun 6. I1 and I2 represent the corresponding spots.

If the scanning law of the object is always the same, it can be recorded once and for all. Only the absorption signal must then be coded, recorded and decoded each time. The nature of the radiation used for the examination is selected as a function of the intended application, the only condition being that the radiation must be capable of being propagated in the form of a fine beam, the precision of the analysis being a function of the width of the beam, as we have seen.

Instead of modulating the intensity of the writing beam (which is the preferred embodiment), it is possible to modulate the rate of displacement of the spot.

What is claimed is:

1. A system for the exploration of an object through scanning said object with a narrow continuous wave radiating beam, radiated by a transmitter transducer and towards a receiver transducer which supplies a reception signal said transducers being located on either side of said object and being synchronously linearly and angularly displaced in order that the beam occupies sets of successive parallel positions, the sets being angularly offset by a pedetermined angle with respect to each other, which results in a full scanning of the object according a given scanning plane and under various angles of attack, said system further comprising:
   a. a device comprising writing means, and recording means including a surface capable of charge storage and of memorization and
   b. further means for making said writing means scan said surface with a scanning law homothetic to the law of scanning of said object with said narrow beam, said writing means supplying a writing beam, focused onto said surface, one of the parameters of said writing beam, velocity or intensity, being modulated by said reception signal, while the other of said parameters is kept constant, and one scan line corresponding to each position of the assembly built up by said transducers.

2. A system according to claim 1, wherein said surface is a remanent luminosity surface.

3. A system according to claim 2, wherein said device is a cathode ray tube of the memory and recording type.

4. A system according to claim 1, wherein said device is an electronic tube of the memory type comprising a target, writing means and reading means having a reading electrode and supplying a reading beam onto said target, said further means being coupled to the writing means of said tube, said system further comprising a visual display tube, coupled to said reading electrode, the spot of said visual display tube being modulated by the signal supplied by said electrode when said target is being struck upon by said reading beam.

5. A system according to claim 4, wherein the scanning law of the target of the memory tube is homothetic with the scanning law of the screen surface of the visual display tube, said system comprising a scan control device coupled in parallel to said memory tube and to said visual display tube.

6. A system according to claim 4, wherein the scanning law of the target of the memory tube is different from the scanning law of the screen surface of the visual display tube, said system comprising a conventional scan control device for said visual display tube supplying a first and a second sawtooth signal, and a scan control device for said reading beam comprising a high frequency oscillator having an output $\pi/2$ phase shifter, and a first and a second sum amplifier having respective first inputs for said first and second sawtooth signal respectively, and second inputs, respectively coupled to said oscillator directly and through said phase-shifter.

7. A system according to claim 1 further comprising dead-memory recording means, having a recording input for receiving said reception signals and an output, and means for selectively coupling said device to the receiver transducer and to said output.

8. A system according to claim 7 wherein said dead-memory recording means is a digital memory device.

9. A system according to claim 7 further comprising a variable gain amplifier inserted in series between said output and said device.

* * * * *